US012667594B2

(12) United States Patent
Ganey et al.

(10) Patent No.: US 12,667,594 B2
(45) Date of Patent: Jun. 30, 2026

(54) HYALURONIC COMPOSITION

(71) Applicant: Vivex Biologics Group, Inc., Atlanta, GA (US)

(72) Inventors: Timothy Ganey, Tampa, FL (US); Harry Thomas Temple, Miami, FL (US); Shabnam Namin, Miami, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 570 days.

(21) Appl. No.: 17/241,412

(22) Filed: Apr. 27, 2021

(65) Prior Publication Data

US 2021/0338742 A1 Nov. 4, 2021

Related U.S. Application Data

(60) Provisional application No. 63/019,639, filed on May 4, 2020.

(51) Int. Cl.
A61K 35/58 (2015.01)
A61K 8/73 (2006.01)
(Continued)

(52) U.S. Cl.
CPC .............. A61K 35/58 (2013.01); A61K 8/735 (2013.01); A61K 8/987 (2013.01); A61K 31/728 (2013.01);
(Continued)

(58) Field of Classification Search
CPC ........ A61K 35/58; A61K 8/735; A61K 8/987; A61K 31/728; A61K 35/32; A61K 35/35;
(Continued)

(56) References Cited

U.S. PATENT DOCUMENTS

| 4,272,522 | A | 6/1981 | Balazs |
| 5,128,326 | A | 7/1992 | Balazs |
| | | (Continued) | |

FOREIGN PATENT DOCUMENTS

| CN | 102108318 | 6/2011 |
| CN | 102232578 | 11/2011 |
| | (Continued) | |

OTHER PUBLICATIONS

Gansau J, Buckley CT. Incorporation of Collagen and Hyaluronic Acid to Enhance the Bioactivity of Fibrin-Based Hydrogels for Nucleus Pulposus Regeneration. J Funct Biomater. Jul. 10, 2018;9(3):43. doi: 10.3390/jfb9030043. PMID: 29996555; PMCID: PMC6164980. (Year: 2018).*

(Continued)

*Primary Examiner* — Bethany P Barham
*Assistant Examiner* — Janet Joseph
(74) *Attorney, Agent, or Firm* — Kilpatrick Townsend & Stockton LLP

(57) ABSTRACT

A composition has hyaluronic acid and one or more materials as an admixture. The hyaluronic acid is derived from a fascia tissue layer of an alligator, the fascia layer located below a hide and above muscle tissue. The one or more materials as the admixture to the hyaluronic acid can be a carrier, diluent or excipient. The hyaluronic acid is extracted from the fascia tissue layer in the form of an oil having an oily viscosity with a molecular weight of 30,000 or greater. The oil extracted includes the hyaluronic acid and includes sodium or salts of hyaluronic acid. The oil extracted is anti-inflammatory to human tissue.

6 Claims, 4 Drawing Sheets

6, 8

4

(51) Int. Cl.

| | |
|---|---|
| *A61K 8/98* | (2006.01) |
| *A61K 9/00* | (2006.01) |
| *A61K 31/728* | (2006.01) |
| *A61K 35/30* | (2015.01) |
| *A61K 35/32* | (2015.01) |
| *A61K 35/35* | (2015.01) |
| *A61K 38/18* | (2006.01) |
| *A61K 38/39* | (2006.01) |
| *A61K 47/02* | (2006.01) |
| *A61K 47/36* | (2006.01) |
| *A61L 26/00* | (2006.01) |
| *A61L 27/10* | (2006.01) |
| *A61L 27/12* | (2006.01) |
| *A61L 27/26* | (2006.01) |
| *A61L 27/36* | (2006.01) |
| *A61L 27/56* | (2006.01) |
| *A61Q 17/00* | (2006.01) |
| *A61Q 19/08* | (2006.01) |

(52) U.S. Cl.
CPC .............. *A61K 35/32* (2013.01); *A61K 35/35* (2013.01); *A61K 38/1841* (2013.01); *A61K 38/39* (2013.01); *A61K 47/02* (2013.01); *A61L 27/10* (2013.01); *A61L 27/12* (2013.01); *A61L 27/26* (2013.01); *A61L 27/3608* (2013.01); *A61L 27/3612* (2013.01); *A61L 27/56* (2013.01); *A61Q 17/005* (2013.01); *A61L 2400/06* (2013.01); *A61L 2400/12* (2013.01); *A61L 2430/06* (2013.01); *A61L 2430/24* (2013.01)

(58) Field of Classification Search
CPC .... A61K 38/1841; A61K 38/39; A61K 47/02; A61K 35/30; A61K 9/0019; A61K 47/36; A61L 27/10; A61L 27/12; A61L 27/26; A61L 27/3608; A61L 27/3612; A61L 27/56; A61L 2400/06; A61L 2400/12; A61L 2430/06; A61L 2430/24; A61L 2300/41; A61L 26/0023; A61L 26/0057; A61L 26/0066; A61L 26/008; A61L 26/0085; A61L 26/0095; A61Q 17/005; A61Q 19/08; C08L 5/08
See application file for complete search history.

(56) References Cited

U.S. PATENT DOCUMENTS

| | | | |
|---|---|---|---|
| 5,294,446 A | 3/1994 | Schlameus et al. | |
| 5,356,629 A | 10/1994 | Sander et al. | |
| 5,925,626 A | 7/1999 | Della Valle | |
| 6,703,377 B2 | 3/2004 | Radomsky | |
| 6,723,706 B2 | 4/2004 | Pressato et al. | |
| 7,691,829 B2* | 4/2010 | Petito ................. | A61L 26/0052 514/56 |
| 9,144,631 B2 | 9/2015 | Asius et al. | |
| 9,675,643 B2 | 6/2017 | Weston et al. | |
| 9,687,511 B2 | 6/2017 | Weston et al. | |
| 10,064,896 B2 | 9/2018 | Temple et al. | |
| 10,413,572 B2 | 9/2019 | Namin et al. | |
| 10,645,921 B2 | 5/2020 | Temple et al. | |
| 2009/0175944 A1* | 7/2009 | Ringeisen ............... | A61L 27/52 424/484 |
| 2013/0052155 A1* | 2/2013 | Marcolongo ............. | C08L 5/10 530/395 |
| 2014/0335046 A1* | 11/2014 | Matheny ................ | A61K 45/06 424/583 |
| 2018/0021138 A1* | 1/2018 | Estes ................... | A61F 2/30756 623/16.11 |
| 2020/0230174 A1 | 7/2020 | Chung et al. | |
| 2021/0386863 A1* | 12/2021 | Hahn .................. | A61K 47/549 |

FOREIGN PATENT DOCUMENTS

| | | | | |
|---|---|---|---|---|
| CN | 105362470 | 3/2016 | | |
| CN | 105362471 | 3/2016 | | |
| CN | 107513461 | 12/2017 | | |
| CN | 108066288 | 5/2018 | | |
| CN | 108467779 | 8/2018 | | |
| CN | 105816358 B | * 5/2019 | ............. | A61K 8/342 |
| CN | 110075356 | 8/2019 | | |
| CN | 110354055 | 10/2019 | | |
| MX | 2008009296 | 1/2010 | | |
| WO | 2021108790 A1 | 6/2021 | | |

OTHER PUBLICATIONS

Alligator Byproducts: A Reservoir of Hyaluronic Acid for Biomedical and Cosmetic Applications, Jack Losso and Jose Daniel Estrada-Andino, 2019 issue of Louisiana Agriculture; https://www.lsuagcenter.com/profiles/lbenedict/articles/ p. 1578694717223.
Louisiana Alligators: From Threatened to Thriving; National Sea Grant NOAA LSU, Jun. 30, 2017; https://www.laseagrant.org/2017/la-alligators-threatened-to-thriving/.

\* cited by examiner 6, 8

2

4

6     4     2

8

22

24

Exponential Pore Size to Surface area

2500000

2000000

1500000

1000000

500000

0

300 micron pore   400 micron pore   500 micron pore   600 micron pore   700 micron pore   800 micron pore pore radius ━━ Pore surface area

HYALURONIC COMPOSITION

RELATED APPLICATIONS

The present application claims benefit from U.S. Provisional Application No. 63/019,639, filed May 4, 2020 which is hereby incorporated by reference in its entirety.

TECHNICAL FIELD

This invention relates to a composition having hyaluronic acid and one or more materials as an admixture.

BACKGROUND OF THE INVENTION

There has been an interest in using hyaluronic acid formulations in a variety of applications such as cosmetics, wound care, inflammatory osteoarthritis, orthopedic cartilage and bone repairs.

Hyaluronic acid (HA) typically has a large molecular weight and can be found naturally occurring in a broad sector of living organisms that spans from microbes to mammals, obtained from food sources such as bone broth, soy-based foods, starchy root vegetables, citrus, and leafy greens, and derived in large amounts by extraction as well as by synthetic chemistry One of the common sources is bovine HA having a molecular weight of $10^4$-$10^5$ Dalton (Da). A more preferred source is rooster comb having a molecular weight of $10^6$-$10^7$ Da. Human umbilical cord also exhibits a molecular weight of $10^6$-$10^7$ Da. Additional efforts have focused on microbial fermentation, but inherent limitations of molecular viscosity have limited the practicality and yield.

Hyaluronic acid naturally occurring non-sulfated glycosaminoglycan (GAG) non-protein compound with distinct physico-chemical properties of repeating β-1,4-D-glucuronic acid and β-1,3-N-acetylglucosamine units. This biochemical moiety is highly hydrophilic due to the large molecular shape and endowed elasticity allows it to carry at least over twenty times or more its weight in water, reportedly capable of attracting up to 1000 times its weight in water. This amazing water retaining feature means a solution with HA can retain moisture in eyes, joints and skin tissue. Hyaluronic acid, as a linear, negatively charged, highly hydrophilic and non-sulfated glycosaminoglycan (GAG) is mainly found in the extracellular matrix in the form of sodium salt. The high molecular weight GAG during the normal course of metabolic processing is degraded by hyaluronidases, chondroitinases, and reactive oxygen species to yield size-dependent polymers with a multitude of signaling properties. There is consensus that larger HA chains have anti-inflammatory properties, and that HA interacts with a variety of cell surface receptors and HA-binding proteins to activate intracellular events that stabilize matrix through water binding properties that maintain elasticity of tissues.

The use of solutions of HA for medical and clinical applications is seeking and trying to advantageously use the unique properties of hyaluronic acid in a variety of novel ways.

The present invention has discovered a source of HA found in reptiles, most particularly alligators or crocodiles. An alligator's body is covered with bony plates called osteoderms or scutes. Advantageously, in the deep fascia underlying the hide or skin and above the muscle tissue, is an abundant amount of HA molecules. It is these HA molecules in combination with other materials that provides a basis for improvement in compositions for use in medical applications in skin treatments, wound care, orthopedic including bone and cartilage repair, and in vertebral disc repair and regenerations as is described hereinafter.

Due to its biocompatibility, biodegradability, non-immunogenicity, water binding properties and cell receptor facilitation, HA has unique applications as a source of biopharmaceutic applications. HA-drug conjugates have been shown to increase solubility, permeability and bioavailability of several anti-cancer and anti-inflammatory drugs, as well as support anti-desiccation and anti-inflammatory processes in advanced wound care. HA features address structural, biosynthetic and biological properties, but source-specific applications unique to the alligator or crocodile composition attend and offer properties that optimize the use and enhance the biologic activity.

SUMMARY OF THE INVENTION

A composition has hyaluronic acid and one or more materials as an admixture. The hyaluronic acid is derived from a fascia tissue layer of an alligator, the fascia layer located below a hide and above muscle tissue. The one or more materials as the admixture to the hyaluronic acid can be a carrier, diluent or excipient. The hyaluronic acid is extracted from the fascia tissue layer in the form of an oil having an oily viscosity with a molecular weight of 30,000 or greater. The oil extracted includes the hyaluronic acid and includes sodium or salts of hyaluronic acid. The oil extracted is anti-inflammatory to human tissue.

The hyaluronic acid can be intermixed with a carrier of a polymer suitable for injection into a joint for repairing subchondral tissue.

The hyaluronic acid exhibits criteria important for biomaterials including biodegradability and bioactivity. While some materials such as bioceramics (including aluminum oxide and zirconium oxide), polymers (including polyurethane and silicone rubber), and biomedical metals (including stainless steel and titanium (Ti) alloys) provide good biocompatibility and/or excellent mechanical strength, the lack of integration imposes a metabolic burden of inert permanence and a constancy of tissue interface that results in interfragmentary strain and excessive fibrosis. In contrast, hyaluronic acid has demonstrated intrinsic osteogenic capacity and anti-inflammatory properties that minimize tissue destruction secondary to inflammation. In this context, the biodegradable and/or bioactive materials, including bioactive ceramics, biodegradable polymers, and trace content of biodegradable metals are considered compositions that can be coupled with HA as an asset separated to structural that is synergistic to strategy.

The hyaluronic acid can be infused in a carrier material of high porosity exhibiting 50% or greater void volume with a variable pore size of 50 to 1000 microns, the carrier material being an osteoconductive/osteoinductive material for inducing bone growth and repair. The high porosity carrier material has a plurality of open cells or pores, some of the open cells are interconnected forming passages through the carrier material, some of the open cells are separated by windows, the windows being of a 10-micron thickness or greater. The composition can be a hyaluronic hydrogel. Alternatively, the composition can be a hyaluronic acid foam. The hyaluronic acid foam further has micro and nano sized ceramic particles. The ceramic particles can be one or more calcium salts including hydroxyapatite, calcium phosphates, silicates, B-TCP tetracalcium phosphate and calcium carbonate. Furthermore, Ca—Si ceramics, including wollastonite $(CaSiO_3)$, akermanite $(Ca_2MgSiO_7)$, diopside $(CaMgSi_2O_6)$, hardystonite $(Ca_2ZnSi_2O_7)$, bredigite $(Ca_7MgSi_4O_{16})$, and merwinite $(Ca_3MgSi_2O_8)$, offer unique formulations that have been shown to enhance and regulate osteogenic and bone mineralization functional properties.

The composition of the hyaluronic acid foam further comprises demineralized bone in the form of fibers and/or particles imbued in the hyaluronic acid foam. The composition further includes acellular biologic materials including one or more of exosomes, vesicles, cell fragments, ligands, lipid rafts, organelles, etc. The composition further can have cartilage particles or cartilage fluff imbued in the foam for use in cartilage tissue repair. The composition further can have growth factors of TGF-b added to the hyaluronic acid foam, as well as material binding insertions and extensions with pro-peptides, lead sequences, or other post-translational modifications including but not limited to phosphorylation, glycosylation, methylation, ubiquitination, or acetylation.

In one embodiment, the composition further has amnion or amniotic fluid or combinations of both. In another embodiment, the composition further has collagen. The composition can be reconstituted as a paste or gel for topical cosmetics, skin treatments or wound care. In yet another embodiment, the composition further has a non-alcohol based germicidal agent for hand sanitization. In yet a further embodiment, the composition further can have one or more pharmaceutical agents or medicines added to the composition, wherein the composition is formed as an injectable. The injectable reduces pain and inflammation.

In one further embodiment, the composition can have micronized nucleus pulposus included into the injectable form used in repair and regeneration of damaged discs.

In other embodiments, the composition can be compounded with nano-fibers of collagen, additional fibers of HA produced by electrospinning, and fractional compositions of HA or collagen with nano- and micro-ceramics, and even cermet combinations that carry both nanometal and nanoceramic synergy.

Additional compositions can include thermostabilized, cryoprotected, cell products including lyophilized platelets, plasma, and cell ghosts including membrane rafts, ligand-enriched membranes, and bioavailable assets of mitochondrial and other cytoplasmic derivatives.

Definitions

As used herein and in the claims:

Hyaluronic acid (HA): is a polysaccharide (Glycosaminoglycans (GAGs) or mucopolysaccharides) that can attract up to 1,000 times its weight in water, HA is known to have a large molecular weight and therefore does not penetrate the skin naturally but can be broken down by a chemical reaction with water, hydrolyzing. Another way to make pure hyaluronic acid a useful topical is to "extract" its "sodium salt" to get sodium hyaluronate. The polyanionic form, commonly referred to as hyaluronan, is a visco-elastic polymer found in the aqueous and vitreous humour of the eye and in the fluid of articulating joints.

Molecular weight is synonymous with molecular mass; however, in common practice, it is also highly variable as are the units used in conjunction with it. Many common preparatory sources use g/mol and effectively define it as a synonym of molar mass, while more authoritative sources use Da or u and align its definition more closely with the molecular mass. Even when the molecular weight is used with the units Da or u, it is frequently as a weighted average similar to the molar mass but with different units. In molecular biology, the weight of macromolecules is referred to as their molecular weight and is expressed in kDa, although the numerical value is often approximate and representative of an average.

A distinct advantage of hydrophilic properties is the mass structuring that accompanies the water absorbance. Hydrophilic metabolites play important roles in cellular energy metabolism, signal transduction, immunity that stem from matrix charge, volume solute equilibrium, and diffusion-osmosis shifts reacting to affinity dynamics; particularly attending polar compounds. A strategy in this regard is to control the mobility of growth factors (GFs) and ensure non-covalent interactions between different parts of the ECM and GFs remain non-directional. Other strategies might append or tether ionic bonds as well as the hydrophobic and polar interactions. However, non-covalent interactions exist that are directional, including for example hydrogen bonds and host-guest interactions that might be accomplished with specific printing, subtraction etching, laser welding, or other field defining electrophysiologic controls that effect the bonding during the precipitation of the hybrid foam, or combination.

Rooster comb injections or treatments are made of a naturally occurring substance called hyaluronic acid that is found in rooster combs (the flesh on top of their head) and injected into or applied to affected joints or tissue to help cushion and lubricate the joints or tissue.

Salt of hyaluronic acid: Sodium hyaluronate is the salt form of hyaluronic acid, which makes it water-soluble and allows it to penetrate the skin deeper. Because it's synthesized to have a smaller molecular structure, it's also more stable and less susceptible to damage from oxidation.

BRIEF DESCRIPTION OF THE DRAWINGS

The invention will be described by way of example and with reference to the accompanying drawings in which.

DETAILED DESCRIPTION OF THE INVENTION

In this detailed description of the present invention, the inventors have proposed uses of hyaluronic acid (HA) derived from a specific source, more particularly, from an alligator or crocodile of the reptilian family.

In North America, there are large numbers of alligators in the southern part of the United States from Florida to Louisiana. It is these particular reptiles that abundant source of hyaluronic acid molecules is found in the deep fascia layers below the hide and surrounding the muscle tissue.

This layer of tissue has extraordinary lubricating properties due to vast quantities of hyaluronic acid molecules. It is this source of alligator derived HA that when combined with other materials provides unique and greatly improved medical compositions for use in a range of treatments for joints, cartilage, tendons, bones, skin, pain, and wound care to name a few.

Figure 1A:
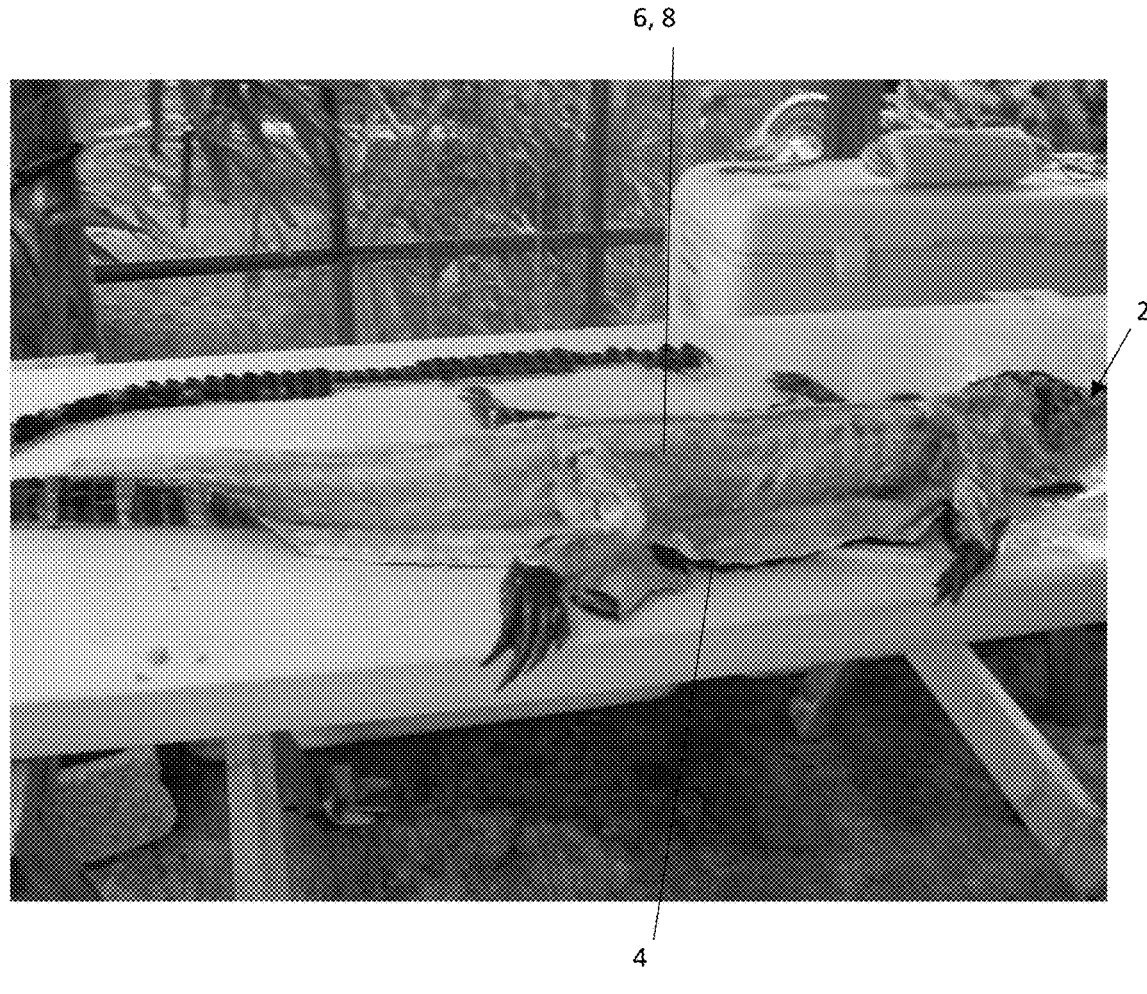
FIG. 1A is a depiction of an alligator with the hide partially removed exposing the deep fascia and muscle tissue.
Figure 1B:
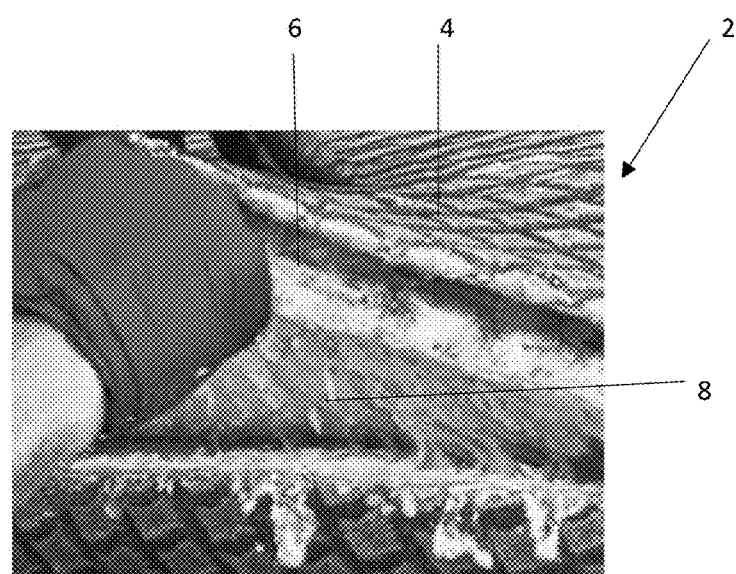
FIG. 1B shows a portion of the hide being peeled or skinned from the carcass.

As shown in FIG. 1A, a representative photograph of an alligator 2 with the hide 4 partially removed exposing the fascia layer 6 which is laden with HA molecules of very high quality for use in medical compositions and the underlying muscle tissue 8 which the fascia layer 6 surrounds. FIG. 1B shows a technician cutting the hide. Once the derma fascia layer is removed it is processed to recover the quantity of HA molecules. Care is taken to prevent oxidation damage during recovery.

The primary source of naturally occurring HA molecules has been rooster comb or bovine or bacterial sources. It has been confirmed that HA from different sources have the same primary structure but different molecular weight. The order of HA molecular weight (Mw) ranges from 104 to 107 Dalton. For example, HA that is isolated from bovine vitreous have a lower molecular weight in the range of 104-105 Dalton, while HA from umbilical cord and rooster comb have a higher molecular weight around 106~107 Dalton. The present invention is directed to using the reptilian source of the alligator due in part to the enhanced molecular performance closely replicating synovial fluids with improved viscoelasticity allowing restorative effects overcoming cartilage biosynthesis and degradation, anti-inflammatory effects, and direct analgesic effects. Further value of the high molecular weight is derived from the water binding and water structuring capabilities of these molecules. The polydisperse distribution of molecular weight in HA sourced from alligator backstrap tissues has been demonstrated at (~15-1100 kDa).

Figure 2:
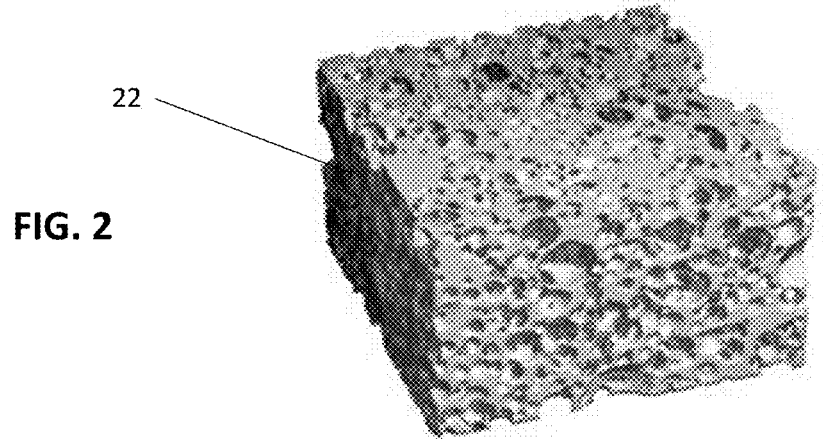
FIG. 2 is an exemplary cube of a porous foam shown in a perspective view.
Figure 3A:
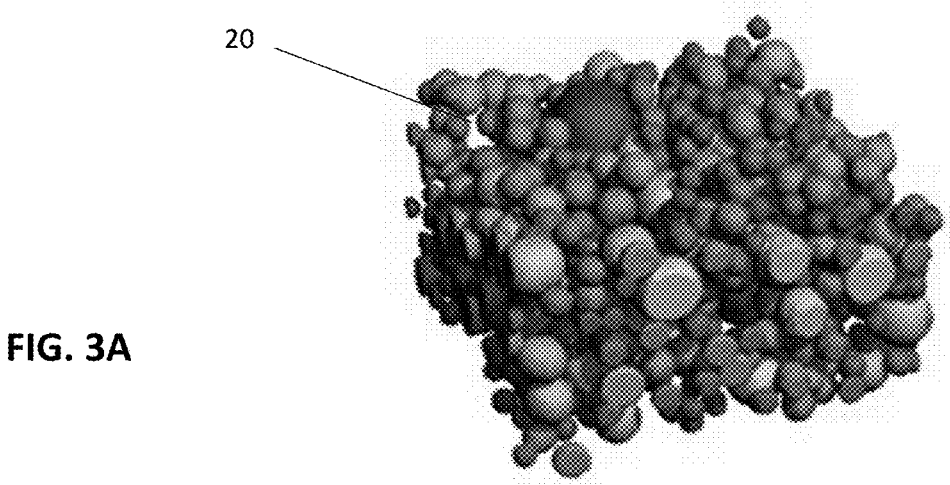
FIG. 3A is a representation of a cube of hyaluronic acid foam structured water image of pores shown in a perspective view.
Figures 3B, 3C:
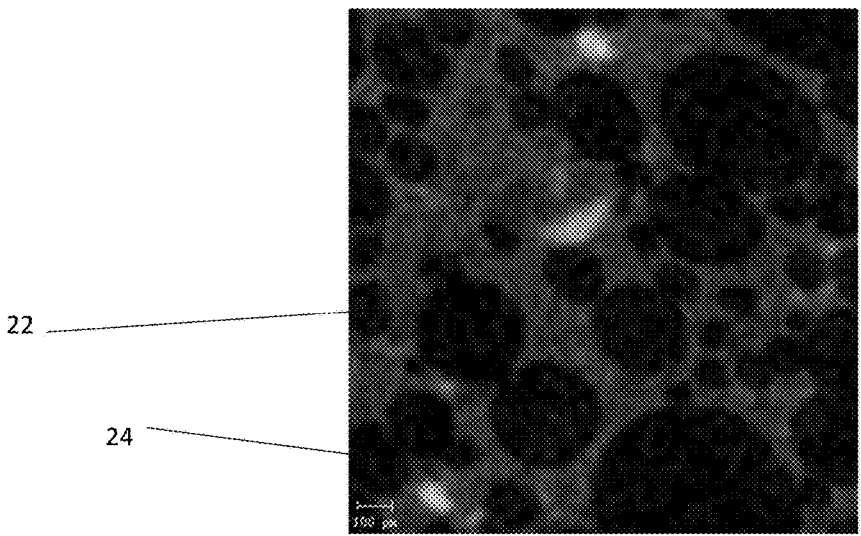
FIG. 3B is an enlarged exemplary view of the pores of molecules taken from FIG. 3A.
FIG. 3C is a graph showing the projected pore size to surface area of the molecule of FIG. 3A.

In FIG. 2, one aspect of the invention is the HA molecules 20 are set in a foam structure 22 that mimics the characteristics of a porous sponge as shown in FIG. 2. The foam structure 22 has pores or an open network of passageways 24 that can be modeled to replicate the trabecular structure of the bone. As shown in FIGS. 3A and 3B, the pores 24 can be open and interconnected or separated by thin permeable windows. When structured as a foam structure 22, the material can be enhanced by the combination of a variety of one or more materials as an admixture to the HA as a carrier, diluent or excipient. Whether structured as a foam or used directly as an oil, the alligator derived HA molecule is ideally suited to be combined to improve a variety of medical compositions. FIG. 3C shows a graph the projected pore size to surface area of the HA molecule.

Interpore Area—Low mag (1000×); High Mag (10,000), Concept: Intercalation; shape, pore in pore, ceramic in varying struts of connected matrix. Pits vs. Posts, Intervariable depth; Intervariable dome Infinitely Hierarchical Variability. Example is to expand to fill pores, and then consolidate tissue as a trabeculated living tissue.

Figure 4:
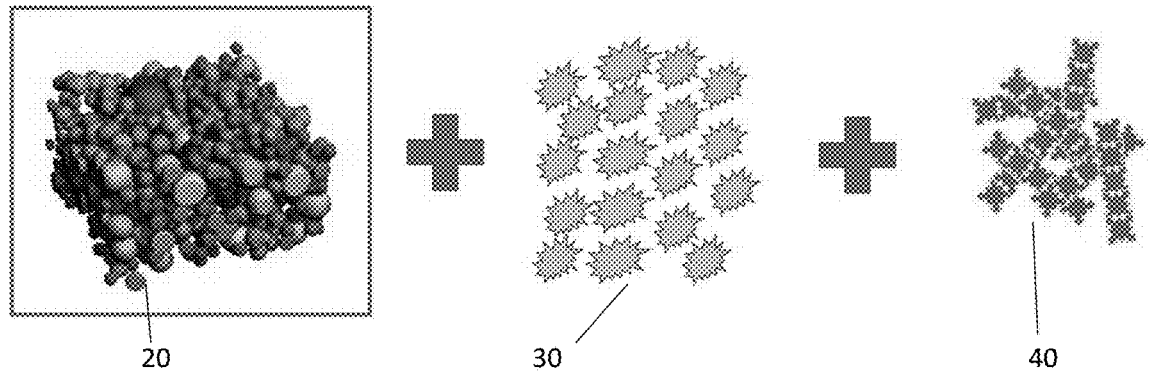
FIG. 4 is a representation showing combinations of HA foam, hydrogel

FIG. 4 is a representative view of HA foam, hydrogel 20 combined as a formulation, additive, admixture with components such as micro and nano ceramics, i.e. hydroxyapatite, calcium phosphates, silicates, etc. 30 or DBM fibers, particulate, exosome imbued, etc. 40. For example, foamed Materials—with additives (i.e. CaCO3), Enhanced Surface Roughness—TCP, Tetra-calcium Phosphate, additive composition.

Cosmetic compositions: The principle characteristics of HA is its ability to retain water. This contributes significantly to the skin maintaining a youthful appearance. The levels of HA in the body decreases with each passing year. As the levels decrease, it adversely impacts the skin's ability to retain moisture, thus leading to inevitable wrinkles. In one aspect of the invention, the use of alligator derived hyaluronic acid supports healthy skin function. Hyaluronic acid helps reproduce healthy skin cells within a collagen matrix by increasing hydration and acting as a lubricant among the collagen matrix of the skin. Hyaluronic acid is an element of the skin's construction and weakens with age, the HA supplements with collagen help ensure ample levels stay in the skin to sustain its overall appearance and function. Accordingly, the benefits of hyaluronic acid are becoming increasingly used an effective anti-aging skin care treatment in the skin care industry. This composition employing a reptilian source greatly enhances this benefit.

Injectable compositions for pain and tissue regeneration. In one aspect of the invention, a purified source of amniotic fluid similar to or the same as described in U.S. Pat. No. 10,413,572 issued on Sep. 17, 2019 is combined with hyaluronic acid derived from alligator deep derma fascia is formed into an injectable. The teachings of U.S. Pat. No. 10,413,572 are being incorporated by reference in its entirety herein. An important aspect of this combination is the HA is an anti-inflammatory which when combined with the amnion fluid is deal for treating pain associated with arthritis, sore joints and muscle injuries. The built-in growth factors in the amnion are tissue regenerative and therefore the combination improves the performance of both.

Bone repair: The composition is particularly useful when the hyaluronic acid derived form an alligator source is combined with bone regenerative materials such as bone particles, bone fibers, mineralized, demineralized, or combinations thereof. The exposure of the HA molecules is supportive of osteoinductivity. Accordingly, such combinations are very useful. In most advanced materials, biologic compositions with or without stem cells can be combined to form the composition. By way of example, materials found in both U.S. Pat. No. 9,675,643"Biologic Composition and Method of Manufacture" and U.S. Pat. No. 9,687,511 "Acellular Biologic Composition and Method of Manufacture", which are being incorporated by reference in their entirety herein, can be combined with HA to create a bone repair material with improved properties.

Spinal Disc Repair: Similarly, the composition can be ideally used in procedures for repairing damaged discs. For way of example, the HA molecules derived from alligators can be combined with nucleus pulposus in a dry powdered form as to create a composition ideally suited for repairing damaged spinal discs. The nucleus pulposus is fully described in U.S. Pat. No. 10,064,896 entitled, "Spinal Disc Regenerative Composition and Method of Manufacture and Use" which is being incorporated by reference herein in its entirety.

In yet another embodiment, the disc repair composition may include stem cells in combination with HA molecules. In U.S. Pat. No. 10,645,921 issuing May 12, 2020 entitled, "Viable Disc Regenerative Composition and Method of Manufacture and Use" which is being incorporated by reference in its entirety, the composition has HA molecules combined with dehydrated micronized nucleus pulposus and bone marrow derived mixture of components, including non-whole cellular components in a biologically compatible, polyampholyte protectant or cryoprotectant. This use of the composition would be similarly protected by the polyampholyte which creates an improved protection of the HA molecules from damage when stored for later use.

As can be seen, the use of the alligator derived HA molecules is not only compatible, but ideally suited for these compositions in a variety of treatments. New advancements have been found wherein exosomes and other acellular biological components can be made into freeze-dried compositions as is taught in co-pending patent application U.S. Ser. No. 16/710,472 entitled "Exosome Composition and Method of Manufacture" and others.

The inventors believe all these new discoveries can be effectively used in combination with the HA molecules derived from alligators without adverse effects.

Various additional benefits of HA of the present invention include: Neutral exothermic foaming, Water structuring, hydrogel capacity, Osteoconductive, Bone-like Geometric Properties, Porosity, Connectivity, Modeling, Non-toxic; Compatible pH, isotonic, non-hemolytic, Negative charge of matrix exceeding that of rooster comb or bacterial expression, Non-hemolytic, isotonic, Aqueous binder of calcium phosphates, hydroxyapatites, open foamed graft extenders, Hybrid composition with bone allografts; i.e. DBM fibers and micronized matrices, Dermal matrices; micronized, fenestrated and compressed, shaped and stamp formed in sheets, suitable for die-cutting and Evolving tension from retraction and modeling of pores, Fiber tension across pores to sustain superstructure, Osteogenesis—bone formation response to tensile forces and stretching, Osteogenesis requires a tension-dependent mechanical cue, Foams of varying sized areas display variations in surface curvature, As matrix surrounding pores dissolves, the internal surface expands in relationship to the pore radius based on a well formulated Surface Area=3.14 (pi)×4×r2, Increasing connectivity based on optimal bone formation from 250-micron through 750-micron porosity, Integrating solid based on open foam consolidation, Bone forms and models to shear; integrating aspects and assets of both tensile and compressive combination Creating differential particle thickness and laminar distribution is also a benefit. Regarding bone, the partially demineralized tissue will be more osteogenic than the less "revealed" particles. If these are also the larger, then the surface area of the larger is exponential to the change in diameter of the particle. If the size is then exposed to stratification, or lamination, or plying, then the larger particles with more surface area are at the bottom. If the HA incorporation allows a strip on the posterior lamina/gutter for fusion, then the greater release of growth factors is near the bone, and a grade percentage of less potential more near the soft tissue surfaces. The benefit is getting bone directed regeneration mesially, and more lateral or peripheral regenerating to the soft tissues supporting them.

HA also incorporates differential buoyance and microcortical variability. The inherent variability in the 100- to 300-micron range for use with materials of many tissue types, such as cartilage, bone, dermis, spinal cord. Assuming a regular distribution of particles produced by the manufacturing, the significant portion will be in the 200-225 um range. The invention takes advantage of the difference in size as a discriminating means of separating and laminating an allogeneic tissue construct. The size of particles can be designed to define a differential stack of matrix where size becomes an extension of angular velocity. Changing radius, speed, and collection allow drying and permit the collection of particles in colloids such as hyaluronic acid. Separating by size can be achieved by vibrational separation during polymerization. Size-varying would be between 100-300 micron. Base vibration tuned to the sizing of the particles.

Screen could be solid as to transmit vibrational alone. Screen could be active sieve to drop materials into standing HA polymerization to separate.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A composition comprising:
   hyaluronic acid obtained from a fascia tissue layer of an alligator, wherein the fascia layer is located below a hide and above muscle tissue, wherein the hyaluronic acid is extracted from the fascia tissue layer in the form of an oil having an oily viscosity with a molecular weight of 30,000 Da or greater, and wherein the extracted oil comprises hyaluronic acid and sodium or salts of hyaluronic acid;
   one or more polymer materials as an admixture to the hyaluronic acid and sodium or salts of hyaluronic acid in the oil as a carrier, diluent, or excipient, wherein the hyaluronic acid is infused in the carrier, diluent, or excipient; wherein the carrier is of high porosity exhibiting 50 or greater void volume with a variable pore size of 50 to 1000 microns; wherein the high porosity carrier has a plurality of open cells or pores; wherein some of the open cells or pores are interconnected forming passages through the carrier; wherein some of the open cells or pores are separated by windows, the windows being of a 10 micron thickness or greater; wherein the carrier is an osteoconductive/osteoinductive material for inducing bone growth and repair;
   wherein the composition is a hyaluronic acid foam that further comprises micro and nano sized ceramic particles selected from a group consisting of hydroxyapatite, calcium phosphates, silicates, B-TCP tetracalcium phosphate, and calcium carbonate, and combinations thereof; and cartilage particles or cartilage fluff imbued in the foam configured for use in cartilage tissue repair.

2. The composition of claim 1, wherein the composition of the hyaluronic acid foam further comprises demineralized bone in the form of fibers and/or particles imbued in the hyaluronic acid foam.

3. The composition of claim 1, wherein the composition further comprises acellular biologic materials including exosomes, vesicles, cell fragments, ligands, lipid rafts, organelles, or a combination thereof.

4. The composition of claim 1, further comprising TGF-b added to the hyaluronic acid foam.

5. A composition comprising:
   hyaluronic acid obtained from a fascia tissue layer of an alligator, wherein the fascia layer is located below a hide and above muscle tissue, wherein the hyaluronic acid is extracted from the fascia tissue layer in the form of an oil having an oily viscosity with a molecular weight of 30,000 or greater, and wherein the extracted oil comprises the hyaluronic acid and sodium or salts of hyaluronic acid; and
   one or more polymer materials as an admixture to the hyaluronic acid and sodium or salts of hyaluronic acid in the oil as a carrier, diluent, or excipient, wherein the one or more polymer materials comprises collagen and amniotic fluid, wherein the composition is reconstituted as a paste or gel configured for use in for topical cosmetics, skin treatments or wound care or hand sanitization.

6. The composition of claim 5, further comprising a non-alcohol based germicidal agent.

\* \* \* \* \*